United States Patent
Wang et al.

(10) Patent No.: US 7,007,542 B2
(45) Date of Patent: Mar. 7, 2006

(54) METHOD OF WARNING OF POISONING IN POISON RESISTANT COMBUSTIBLE GAS SENSORS

(75) Inventors: Chuan-Bao Wang, Oakdale, PA (US); Beth Tomasovic, Cranberry Township, PA (US); P. Richard Warburton, Moon Township, PA (US); Annie Q. Wang, Pittsburgh, PA (US)

(73) Assignee: Industrial Scientific Corporation, Oakdale, PA (US)

(*) Notice: Subject to any disclaimer, the term of this patent is extended or adjusted under 35 U.S.C. 154(b) by 217 days.

(21) Appl. No.: 10/461,366

(22) Filed: Jun. 16, 2003

(65) Prior Publication Data

US 2006/0019402 A1    Jan. 26, 2006

Related U.S. Application Data

(62) Division of application No. 09/771,882, filed on Jan. 30, 2001.

(51) Int. Cl.
*G01D 18/00* (2006.01)
*G01N 19/00* (2006.01)
*G01N 33/497* (2006.01)
*G01N 25/00* (2006.01)
*G01N 7/00* (2006.01)

(52) U.S. Cl. .............. 73/23.21; 73/1.01; 73/1.02; 73/23.2; 73/23.23; 73/23.31; 73/23.32; 422/83; 422/94; 422/95; 422/96; 422/97; 422/98; 29/592; 29/592.1; 29/593

(58) Field of Classification Search ............... 422/95, 422/96, 97, 98, 94, 83; 73/1.01, 1.02, 23.2, 73/23.31, 23.32, 23.21, 23.23; 29/592, 592.1, 29/593
See application file for complete search history.

(56) References Cited

U.S. PATENT DOCUMENTS

| | | | |
|---|---|---|---|
| 4,246,228 A * | 1/1981 | Jones et al. ............. | 422/94 |
| 5,061,447 A * | 10/1991 | Ono ...................... | 422/96 |
| 5,368,713 A * | 11/1994 | Friese et al. ........... | 204/429 |
| 5,401,470 A * | 3/1995 | Poli ...................... | 422/96 |

* cited by examiner

*Primary Examiner*—Brian J. Sines
(74) *Attorney, Agent, or Firm*—Dennison, Schultz, Dougherty & MacDonald

(57) ABSTRACT

A poison resistant combustible gas sensing element, a method for its production and a method for determining poisoning of the element. The element includes an electric heating element, an inner layer coated on the electric heating element and containing a precious metal catalyst supported on a porous oxide, the precious metal catalyst catalyzing combustion of a combustible gas to be detected by the element, and an outer layer overlaying the first layer, and containing a catalytic compound capable of trapping gases which poison the precious metal catalyst, the catalytic compound being supported on a porous oxide.

5 Claims, 8 Drawing Sheets

METHOD OF WARNING OF POISONING IN POISON RESISTANT COMBUSTIBLE GAS SENSORS

This application is a division of Ser. No. 09/771,882 filed Jan. 30, 2001.

BACKGROUND OF THE INVENTION

1. Field of the Invention

The invention relates to combustible gas sensors, and more particularly to a combustible gas sensor with improved resistance to catalyst poisons. The invention also relates to a method for warning if a sensor has been exposed to a catalyst poison.

2. Description of Related Art

Catalytic bead combustible gas sensors have been widely used in industry to detect the presence of combustible gases and vapors for safety purposes and to provide a warning of potentially hazardous conditions before these gases and vapors reach explosive levels. Commercial catalytic bead sensors detect gases through the use of electrically heated helical filaments typically embedded within an oxide material such as alumina, silica, or thoria. A complete gas sensor is composed gas-sensing element and a compensating element, which are typically arranged in a Wheatstone bridge circuit. The gas-sensing element is formed by dispersing a precious metal catalyst such as palladium or platinum on the surface of the metal oxide to catalyze the combustion of the combustible gases. A compensating element is made so that combustible gases do not burn on its surface, but is placed in the circuit for the purpose of compensating for environmental effects such as humidity and ambient temperature, which affect both the gas-sensing and compensating elements. Such a combustible gas sensor is claimed and described, for example, in U.S. Pat. Nos. 3,200,011, 3,092,799, 4,313,907 and 4,416,911, and in Mosley, P. T. and Tofield, B. C., Solid State Gas Sensors, Adams Hilger Press, Bristol, England (1987).

A fundamental problem that arises in using this technology is that the precious metal catalyst is susceptible to poisoning or inhibition by certain compounds commonly present in workplace atmospheres. Examples of such compounds include organosilicons (e.g. hexamethyldisiloxane, decamethyl-cyclopentasilane), organoleads (e.g. tetraethyl lead), organophosphates (e.g. tributyl phosphate), sulfur-containing compounds (e.g. hydrogen sulfide), and halogenated hydrocarbons (e.g. carbon tetrachloride, trichloroethylene). Considerable research has been conducted in an attempt to alleviate the effects of catalyst poisons or inhibitors. Inert porous materials have been used to filter out the poisoning or inhibiting materials that have a relatively large molecular size. These filter materials are either incorporated into the gas-sensing element or applied as an external filter located in the path of gas diffusion.

U.S. Pat. Nos. 4,111,658 and 4,246,228 disclose a gas sensing element which is formed from a catalyst-loaded zeolite or a uniform mixture of oxidation catalyst particles and zeolite particles. The small pore diameters of zeolites (3 to 9 angstroms) allow catalyst poisons or inhibitors to diffuse relatively slowly into the inner part of the gas-sensing element compared to low molecular weight combustible gases such as methane, and thus the poisons are adsorbed and trapped by the zeolite particles to avoid rapid catalyst poisoning or inhibiting. U.S. Pat. No. 4,123,225 describes a sensing element that is provided with an outer layer of a non-catalytic porous material, which tends to prevent non-volatile poisoning residues from reaching catalytically active regions of the gas-sensing element. U.S. Pat. No. 4,560,585 also discusses the preparation of a sensing element using non-catalytic porous aluminum oxide and supported catalyst to build separate and alternating layers to obtain a poison resistant combustible gas sensor. The problem arising from this approach is that typical non-catalytic materials have only weak acid, base, or redox sites and thus do not trap poisons or inhibitors effectively. A thick layer of a non-catalytic material is necessary to filter out poisoning materials effectively but this configuration results in an increase in power consumption and a decrease in sensitivity and thus stability.

European Patent Application No. EP094863 and PCT published application WO 00/43765 disclose gas-sensing elements which are surrounded by a powdered zeolite or porous insulating materials such as silica and alumina. This method is very close to an external filter approach, where a gas sample passes through a separate filter that contains suitable materials such as active charcoal before it reaches the gas-sensing element. However, the gas-sensing element with an external filter has difficulty in detecting alcohols, ketones and combustible gases with a high molecular weight, such as hydrocarbons above heptanes, since the filter also blocks these combustible gases.

When a combustible gas sensor becomes poisoned, it loses sensitivity to the combustible gas or gases that it was designed to measure. Usually, this poisoned condition is not noticeable until the sensor is tested with test gases. Because combustible gas sensors are often used in ambient air environments where there can be no control over the types of poisoning materials that might be encountered, users are required to manually check sensor operation on a regular schedule. Since a sensor can be poisoned quickly when exposed to a poison-containing environment, frequent checking is needed to ensure the integrity of a detection system.

A number of patents have addressed this problem. For example, U.S. Pat. No. 3,960,495 discloses a method of continuously supplying a controlled small amount of a combustible gas or vapor to the vicinity of a gas sensor; inoperativeness of the gas sensor due to poisoning or malfunctioning is observed when the sensor ceases to indicate the presence of at least the controlled small amount of combustible gas or vapor. PCT published application WO 99/17110 discloses an assembly for verifying the response of a combustible gas sensor through the use of a hydrogen generator in an explosion proof housing of a combustible gas sensor. However, this method requires a hydrogen generator to be embedded in the sensor housing, which is not suitable for portable gas detection instruments due to size constraints. Furthermore, hydrogen and organic vapors are not ideal combustible gases to check whether a sensor has been poisoned since they are among the most easily combustible gases, and therefore their responses to the sensor are least affected by poisons.

SUMMARY OF THE INVENTION

It is therefore an object of the invention to provide a gas-sensing element that has an intrinsic resistance to poisoning greater than a conventional gas-sensing element.

It is another object of the invention to provide a sensor which enables the user to easily determine when poisoning has occurred.

It is still a further object of the invention to provide a combustible gas sensor which warns of poisoning without supplying any combustible gas or vapor.

To achieve these and other objects, the invention is directed to a gas-sensitive element comprising an electric heater (e.g. wire filament, thick film, or micromachined thin film), an inner layer of a porous oxide-supported precious metal catalyst that catalyzes combustion of combustible gases and an outer layer of a porous oxide-supported catalytic material that is chemically active in trapping catalyst poisons.

The oxide-supported catalytic materials for the outer layer of the gas-sensing element include four catalyst types:

(1) oxide-supported metal oxides, such as the oxides of vanadium (V), chromium (Cr), manganese (Mn), iron (Fe), cobalt (Co), nickel (Ni), copper (Cu), molybdenum (Mo), tin (Sn), antimony (As), lead (Pb), bismuth (Bi), ruthenium (Ru), cadmium (Cd), rhenium (Re), osmium (Os), and iridium (Ir), supported on porous oxide supports such as alumina ($Al_2O_3$), silica ($SiO_2$), zirconia ($ZrO_2$), and yttrium (Y)—, cerium (Ce)- and lanthanum (La)-stabilized zirconia ($ZrO_2$);

(2) solid acids, preferably solid superacids, such as tungsten oxide/zirconia ($WO_x/ZrO_2$), sulfated zirconia ($SO_4^{2-}/ZrO_2$), niobium oxide ($Nb_2O_5$), silica-alumina ($SiO_2$—$Al_2O_3$), mesoporous aluminosilicates, mesoporous sulfated zirconia, and acid-activated clays;

(3) solid bases, preferably solid superbases, such as magnesia (MgO), alkaline (lithium, sodium, potassium, and cesium)-doped alumina or alkaline-doped zeolites; and (4) metal-loaded zeolites and clays: V, Cr, Mn, Fe, Co, Ni, Cu, Mo, Ru, Cd, Re, Os, Ir-loaded zeolites and clays.

One or more of the above catalytic materials is used to form the outer layer of the gas-sensing element.

The above porous oxide-supported catalytic materials are not conventional combustion catalysts and are thus substantially not active towards combustion of combustible gases such as methane, one of the most inert combustible gases. However, they provide strong redox (reducing/oxidizing), acidic, or basic sites, which are active enough to react with and trap catalyst poisons and to prevent the poisons from diffusing into the inner layer to poison combustion catalyst. Therefore, the gas-sensing element in accordance with the invention provides excellent long-term stability towards methane detection since a catalytic bead combustible gas sensor tends to decrease its sensitivity to methane much more than its sensitivity to other combustible gases after being poisoned.

According to the invention, the gas-sensing element can be small in size, but still retains good poison resistance. Due to the protection of the outer layer against catalyst poisons, the precious metal catalyst content in the inner layer can be minimized. Therefore, the invention provides a gas-sensing element that provides a substantial improvement in poison resistance, lifetime, shock resistance, and power consumption.

According to the invention, it is preferred that the active components in the porous oxide-supported catalytic materials for the outer layer of the gas-sensing element should be loaded onto the oxide support before coating by conventional methods such as impregnation, co-precipitation, ion exchange, and solid diffusion, followed by calcination at 500–700° C. to convert the salts into stable metal oxides supported on the porous oxides. Subsequently, the outer layer of the gas-sensing element is formed by coating the inner layer with a slurry of one of the oxide supported catalytic materials or combinations thereof.

The outer layer formed by a porous oxide-supported catalytic material in accordance with the invention can trap catalyst poisons much more effectively than the layer formed by a non-catalytic material described in U.S. Pat. Nos. 4,123,225 and 4,560,585. It is well known that non-catalytic support materials such as alumina and silica contain only weak or very weak acidic, basic, and/or redox sites that can weakly bind with poisoning compounds such as hexamethyldisiloxane (HMDS). The invention provides porous oxide-supported catalytic materials that contain strong redox, acidic, or basic sites, which are chemically active and effective in trapping poisoning materials such as hexamethyldisiloxane (HMDS) and tetraethyl lead.

The sensor of the invention also provides a method for warning that a sensor has been poisoned by determining a baseline drift when a catalytic bead sensor is exposed to poisons present in ambient air. This approach is both inexpensive and effective, and it is not necessary to expose the sensor to a combustible gas to ascertain if poisoning has occurred.

The sensors made according to the invention generally possess a negative baseline drift when exposed to poisons, due to the differential resistance change rates for the gas-sensing element and the compensating element when exposed to poisoning materials. Because the gas-sensing element traps much more of the poisoning materials than does the compensating element. The deposits formed from the poisoning materials can build up quickly and remain on the gas-sensing element at a relatively high rate, which causes an increase in the total mass of the sensing element and a decrease in the baseline of the whole sensor.

In order to warn of poisoning, a combustible gas sensor frequently compares zero output with a predetermined standard value. Upon determination of a significant deviation between the output and the predetermined standard value within a given period of time, an alarm and display are provided if the deviation is not within a predetermined limit. The invention provides a simple and cost-effective diagnostic of poisoning in a combustible gas detection device.

DESCRIPTION OF THE PREFERRED EMBODIMENTS

Figure 1:
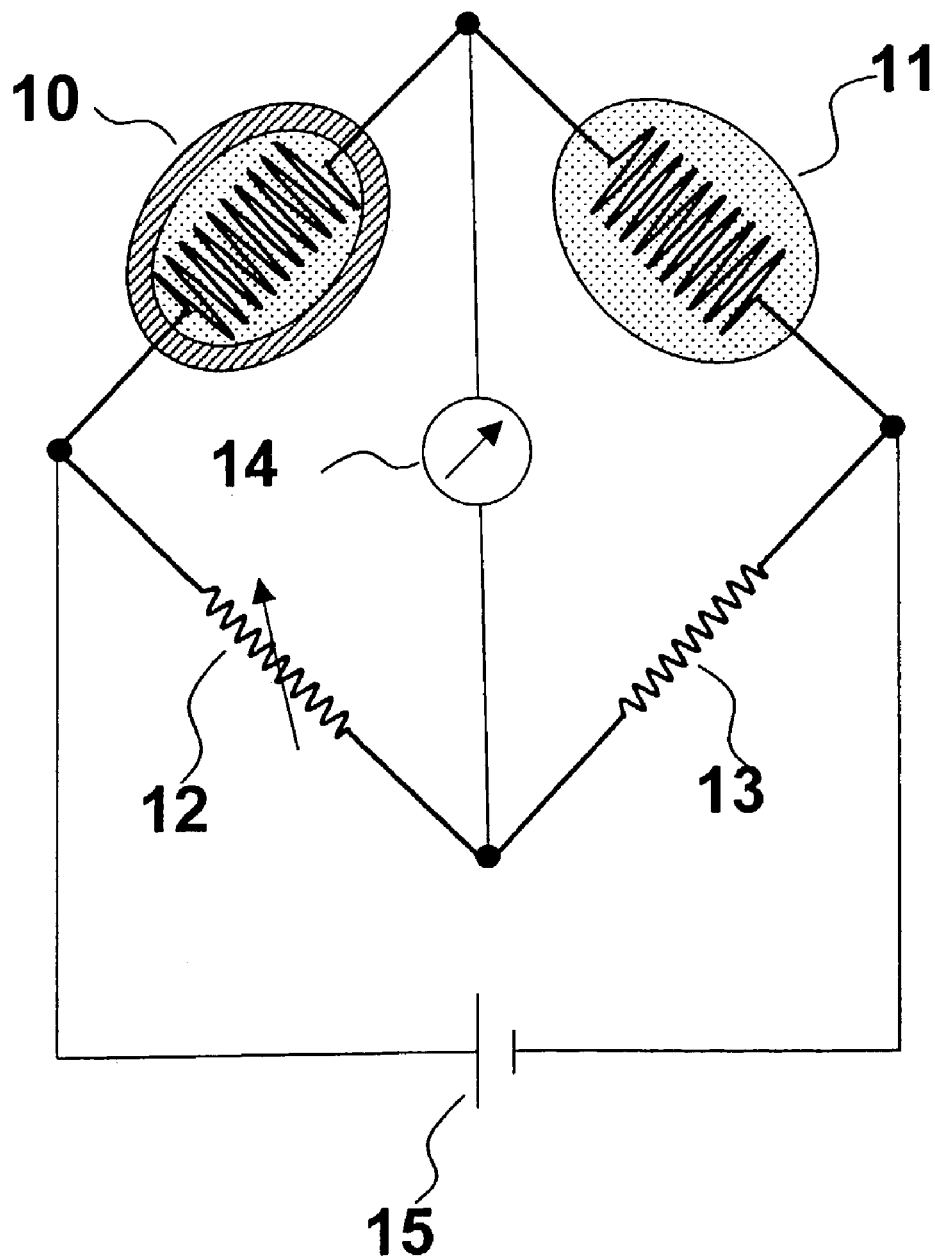
FIG. 1 is a schematic diagram of a Wheatstone bridge circuit in which a gas-sensing element according to the invention and a compensating element are placed.

As shown in FIG. 1, a gas-sensing element 10 is connected in one arm of a Wheatstone bridge circuit, the other three arms being constituted by a compensating element 11, a variable resistor 12, and a fixed resistor 13 having a value such that the bridge can be balanced by adjustment of variable resistor 12. Across the two diagonals of the bridge are respectively connected a voltmeter 14 and a voltage source 15. The output voltage of the source 15 is chosen so as to heat the gas-sensing element 10 and the compensating element 11 to a desired operating temperature. The variable resistor 12 is adjusted so that the voltmeter 14 indicates a zero reading when the gas-sensing element 10 and the compensating element 11 are exposed to normal atmosphere. The gas-sensing element 10 and the compensating element 11 are calibrated to indicate a known combustible gas concentration and then exposed to the atmosphere that is required to monitor.

At the operating temperature, any combustible gas present in the atmosphere will catalytically burn on the surface of the gas-sensing element 10 but not on the surface of the compensating element 11, causing the temperature of the gas-sensing element 10 to rise with a consequent change in its resistance. This increase in resistance causes a change in the potential across the voltmeter 14, which then provides a measure of combustible gas concentration in the atmosphere. Except for the nature of the gas-sensing element 10, the arrangement is well known in the art and therefore need not be described in further detail herein. Alternatively, other circuits can also be used for connecting the gas-sensing element 10 and the compensating element 11, such as other forms of Wheatstone bridge circuits, or equivalents such as the Anderson loop described in Anderson, K. F., ISA-Tech 97, Anaheim, Calif., October 1997.

Figure 2:
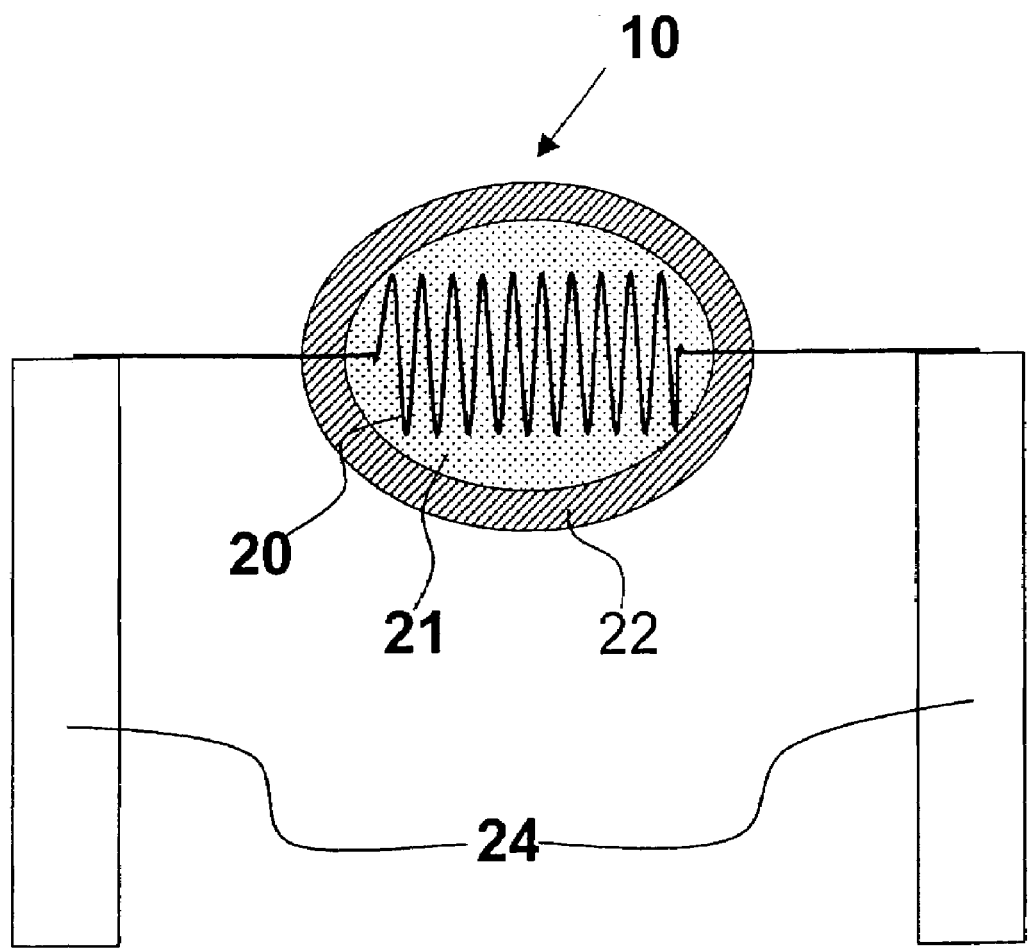
FIG. 2 is a sectional view of a gas-sensing element according to the invention comprising a helical filament embedded in an inner layer of a porous oxide-supported precious metal catalyst and an outer layer of a porous oxide-supported catalytic material.

In a preferred embodiment of the invention shown in FIG. 2, a gas-sensing element 10 comprises a heating element in the form of an electrical resistance filament 20 having leads soldered to a pair of support posts 24. The gas-sensing element is surrounded by an inner layer 21 of a porous oxide-supported precious metal catalyst that catalyzes the combustion reaction, and an outer layer 22 of a porous oxide-supported catalytic material that effectively traps catalyst poisons. The gas-sensing element in accordance with the invention possesses high resistance to poisoning, which is believed to be due to the major portions of the poisons being trapped in the sacrificial outer layer 22 of the active catalytic materials. This results in the subsequent oxidation catalyst layer 21 remaining active to catalyze the combustion of combustible gases.

The inner layer 21 is formed by coating on the electric resistance filament 20 a mixture of at least one porous oxide support material (for example, alumina, silica, zirconia, and/or cerium-, lanthanum-, or yttrium-stabilized zirconia) and at least one catalyst precursor (for example, palladium chloride, hexachloroplatinic acid, and/or rhodium chloride) by conventional means. Upon heating of the filament 20 by passing a current through the filament, the catalyst precursor is decomposed into precious metal oxide, which is finely dispersed on the porous oxide support surface. The inner layer may be formed by applying multiple coats. The inner layer 21, which is the critical portion of the gas-sensing element to catalyze combustion of combustible gases, preferably has a minimal catalyst content so that the catalyst is in as finely dispersed a state as possible on the porous oxide support surface, effectively to prevent deactivation due to agglomeration and sintering of catalyst particles during its conditioning and use, a large number of active sites thereby being available for catalytic reaction. Many other methods for the formation of the gas-sensing element in catalytic bead sensors are well known in the prior art, and these alternate methods can readily be employed in place of the method described herein.

The outer layer 22 of a porous oxide-supported catalytic material is further applied to completely surround the inner layer 21 of the porous oxide-supported precious metal catalyst. The outer layer 22 is formed by coating the inner layer 21 with a slurry of a porous oxide-supported catalytic material with subsequent heating. The outer layer is preferably formed by applying more than one coat.

The porous oxide-supported catalytic materials used for the outer layer 22 in this invention can be divided into four types:

(1) oxide-supported metal oxides, such as vanadium (V), chromium (Cr), manganese (Mn), iron (Fe), cobalt (Co), nickel (Ni), copper (Cu), molybdenum (Mo), tin (Sn), antimony (As), lead (Pb), bismuth (Bi), ruthenium (Ru), cadmium (Cd), rhenium (Re), osmium (Os) and iridium (Ir) oxides supported on porous oxide supports such as alumina ($Al_2O_3$), silica ($SiO_2$), zirconia ($ZrO_2$), and yttrium (Y)—, cerium (Ce)-, and lanthanum (La)-stabilized zirconia ($ZrO_2$)

(2) solid acids, preferably solid superacids, such as tungsten oxide/zirconia ($WO_x/ZrO_2$), sulfated zirconia ($SO_4^{2-}/ZrO_2$), niobium oxide ($Nb_2O_5$), silica-alumina ($SiO_2$—$Al_{2O3}$), mesoporous aluminosilicates, mesoporous sulfated zirconia, and acid-activated clays;

(3) solid bases, preferably solid superbases, such as magnesia (MgO), alkaline (lithium, sodium, potassium, and cesium)-doped alumina and alkaline-doped zeolites; and (4) metal-loaded zeolites and clays: V, Cr, Mn, Fe, Co, Ni, Cu, Mo, Ru, Cd, Re, Os, Ir, Pd, Rh, Pt-loaded zeolites and clays.

One or more of the above catalytic materials are used to form the outer layer 22.

The porous catalytic materials of Type (1) primarily provide strong redox (reducing/oxidizing) surface sites. The catalytic materials of Type (2) provide strong acidic sites and the catalytic materials of Type (3) provide strong basic sites. The catalytic materials of Type (4) provide both strong redox and acidic sites. These strong active sites are believed to be chemically active in trapping poisoning materials inside the outer layer 22.

With regard to the catalytic materials of Type (4), the invention differs from the disclosure of U.S. Pat. Nos. 4,111,658 and 4,246,228, in which a catalyst-loaded zeolite is used to form the entire gas-sensing element. Compared to amorphous porous oxides, zeolites have relatively poor thermal stability and are susceptible to gradual damage of their crystalline structure at temperatures typically applied to catalytic combustible gas sensors. Therefore, sensors made from zeolites generally possess poor sensitivity and baseline stability due to the gradual damage of the crystalline structure at high temperature. This significantly limits their applications to commercial catalytic combustible gas sensors. The invention substantially alleviates this problem by using metal-loaded zeolites only in the outer layer of a gas-sensing element, where the temperature is lower than the inner layer due to thermal gradients, and thus the crystalline structure of zeolites will not tend to be damaged. Furthermore, the metal-loaded zeolites of the invention provide strong acidic sites as well as strong redox (reducing/oxidizing) sites, which are believed to be chemically active in trapping poisons.

It is necessary that prior to making a slurry and coating the inner layer 21, the active components in the porous oxide-supported catalytic materials for the outer layer 22 should be loaded first by conventional methods such as impregnation, ion exchange, co-precipitation or solid diffusion, followed by calcination to convert the salt precursors to metal oxides or solid acid/base species to be immobilized on the surface of porous oxide supports.

It should be emphasized that an outer layer 22 that is effective in trapping poisons allows the inner layer 21 to have low catalyst content and to obtain finely dispersed catalyst particles on oxide supports to prevent the catalyst from agglomerating and sintering during manufacture and use. The outer layer 22 with a relatively high content of active components acts as a sacrificial layer to react with and trap poisoning materials, and the inner layer 21 remains active to catalyze oxidation of combustible gases. The gas-sensing element in accordance with the invention therefore has a great number of active catalytic sites available for catalytic oxidation of combustible gases to take place. The result is that the gas-sensing element in accordance with the invention has a lifetime longer than those of conventional design, principally due to its greater resistance to poisoning and sintering. Furthermore, the gas-sensing element in accordance with the invention can be smaller in size due to its superior poison resistance, so that its power consumption can be lowered and its shock resistance can be improved.

It is well known that catalytic bead combustible gas sensors tend to decrease in sensitivity to methane much more than sensitivity to other combustible gases after they are poisoned because methane is one of the most inert combustible gases. The gas sensing element in accordance with the invention provides excellent long-term stability towards methane detection since the poisoning materials are primarily trapped by the outer layer 22 that are substantially not active in catalyzing methane combustion and the inner layer 21 retains its activity towards methane combustion.

Figure 3:
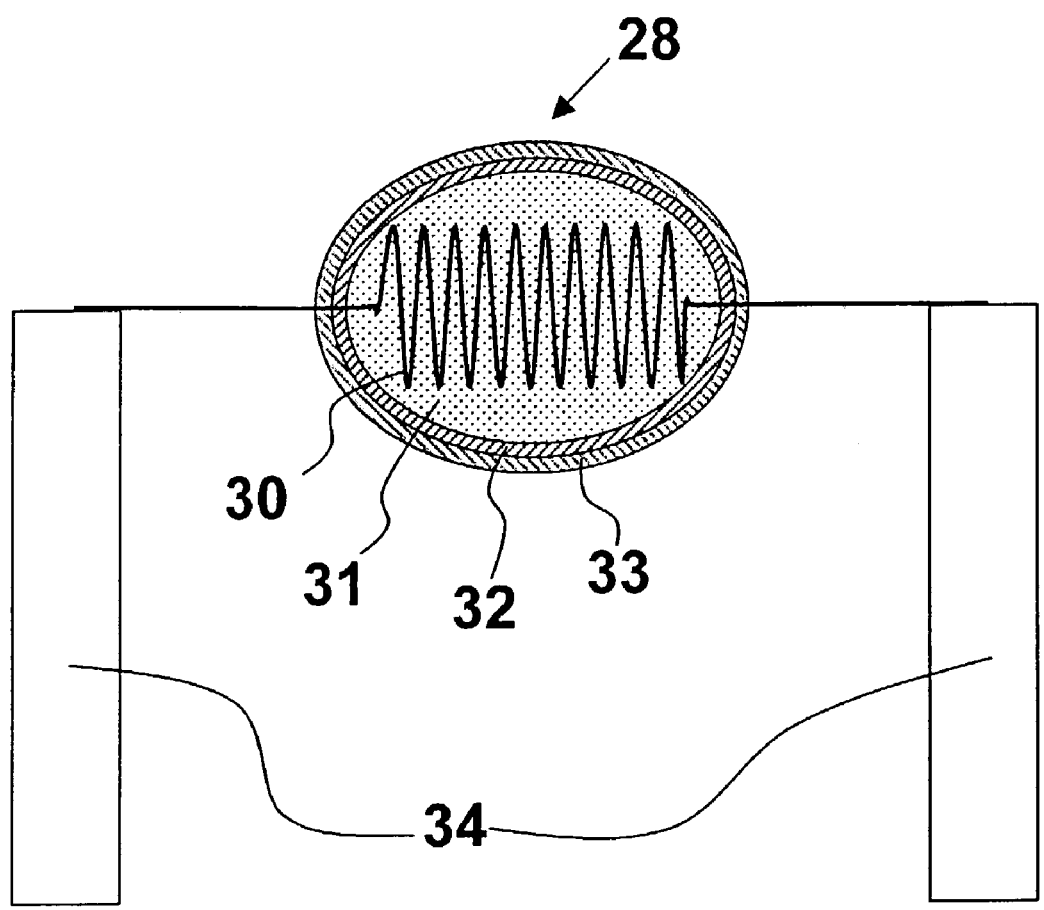
FIG. 3 is a sectional view of a gas-sensing element according to the invention comprising a helical filament embedded in an inner layer of a porous oxide-supported precious metal catalyst and alternating outer layers of different porous oxide-supported catalytic materials.

In another embodiment of the invention, as shown in FIG. 3, a gas-sensing element 28 comprises an electrical resistance filament 30 surrounded by an inner layer 31 of a porous oxide-supported precious metal catalyst and then by sequential outer layers 32 and 33 of different porous oxide-supported catalytic materials. Alternatively, the alternating layers can also be layers of a porous oxide-supported precious metal catalyst 31 and a porous oxide-supported catalytic material 32, or layers of a porous oxide-supported catalytic material 32 and a non-catalytic porous material.

Figure 4:
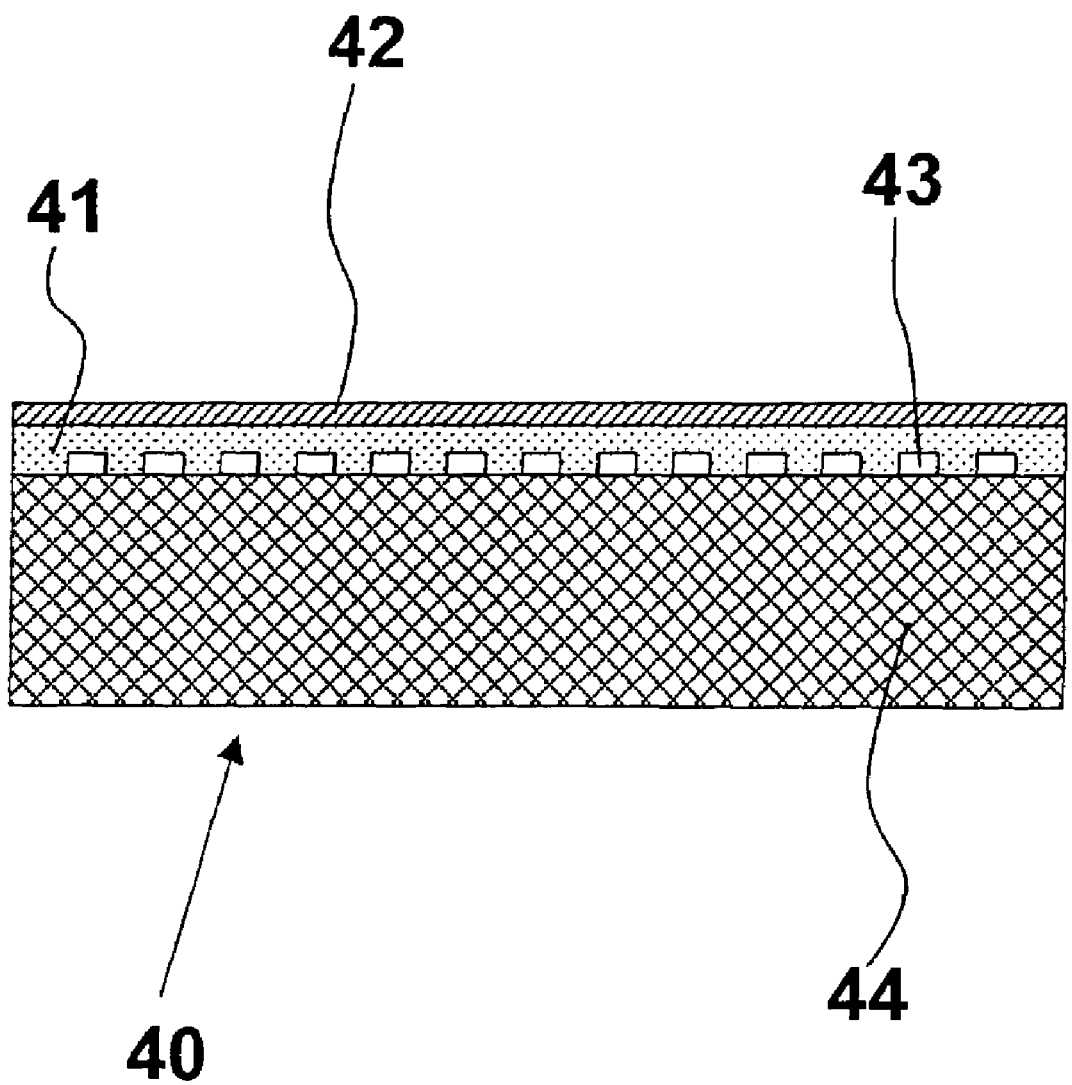
FIG. 4 is a sectional view of a gas-sensing element according to the invention comprising an electric film heater embedded in an inner layer of a porous oxide-supported precious metal catalyst and an outer layer of a porous oxide-supported catalytic material.

In another embodiment of the invention, as shown in FIG. 4, a gas-sensing element 40 is of the planar film type, where an inner layer 41 of a porous oxide-supported precious metal catalyst and an outer layer 42 of a porous oxide-supported catalytic material are deposited on a film heater 43 and a substrate 44. Such a gas-sensing element can be fabricated by thick or thin film technology, such as screen-printing and micro-machining. Examples of planar film sensors are described in Debéda, H., Rebière, D., Pistré, J. and Ménil, F., Sensors and Actuators B, 26–27, 297–300 (1995), and Zanini, M., Visser, J. H., Rimai, L., Soltis, R. E., Kovalchuk, A., Hoffman, D. W., Logothetis E. M., Bonne, U., Brewer, L., Bynum, O. W. and Richard, M. A., Sensors and Actuators A, 48, 187–192 (1995). This embodiment of the invention is substantially different from the disclosure of U.S. Pat. No. 4,911,892, in which a catalytic combustion filter containing precious metal catalyst is integral with a gas-sensing film for minimizing the effect of interference gases, to increase sensitivity to a specific gas in a semiconductor-sensing device.

Figure 5:
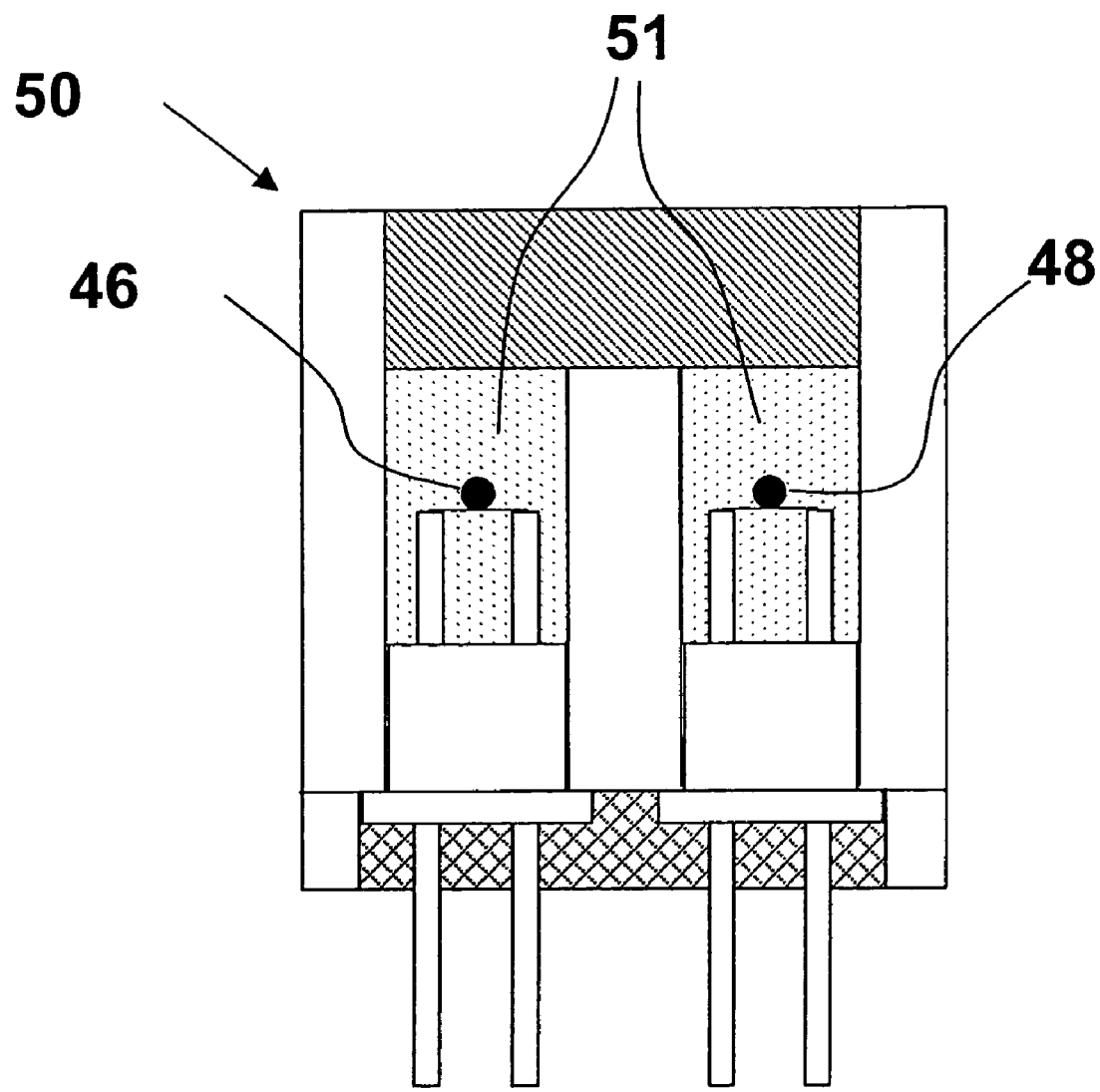
FIG. 5 is a sectional view of a sensor with a gas-sensing element according to the invention and a compensating element completely surrounded by a porous oxide-supported catalyst material powder.

In another embodiment of the invention, the porous oxide-supported catalytic materials can be in powder form. As shown in FIG. 5, a gas-sensing element 46 and a compensating element 48 of a sensor 50 are completely surrounded by porous oxide-supported catalytic materials 51 in powder form, as disclosed in European Patent Application No. EP0094863 and PCT published application WO 00/43765.

Figure 6:
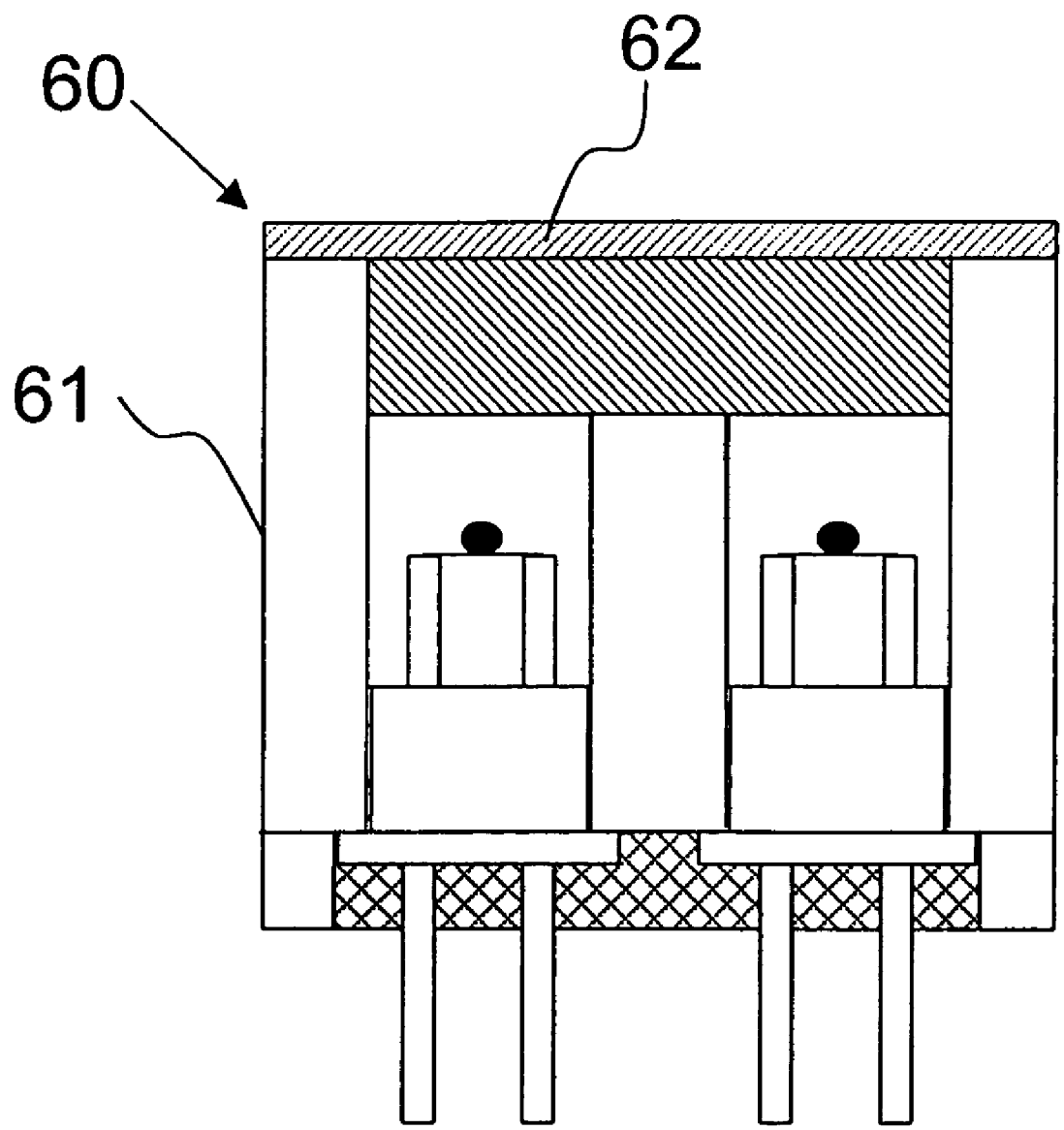
FIG. 6 is a sectional view of a sensor with an external filter.

In another embodiment of the invention, the porous oxide-supported catalytic materials are used to form an external filter, which is placed in the path of gas diffusion to trap catalytic poisons. FIG. 6 shows a sensor 60 having an external filter 62 placed at the top of sensor housing 61. Alternatively, the filter can be placed within the sensor housing. The external filter can be in any conventional form, such as supported on paper, blank, and monolith. When the porous oxide-supported catalytic materials are used as external filters, the calcination temperature of 500–700° C. may or may not be applied when preparing these materials. When calcination at high temperature is not applied, the active components are in the form of salt precursors supported on porous oxide supports.

Figure 7:
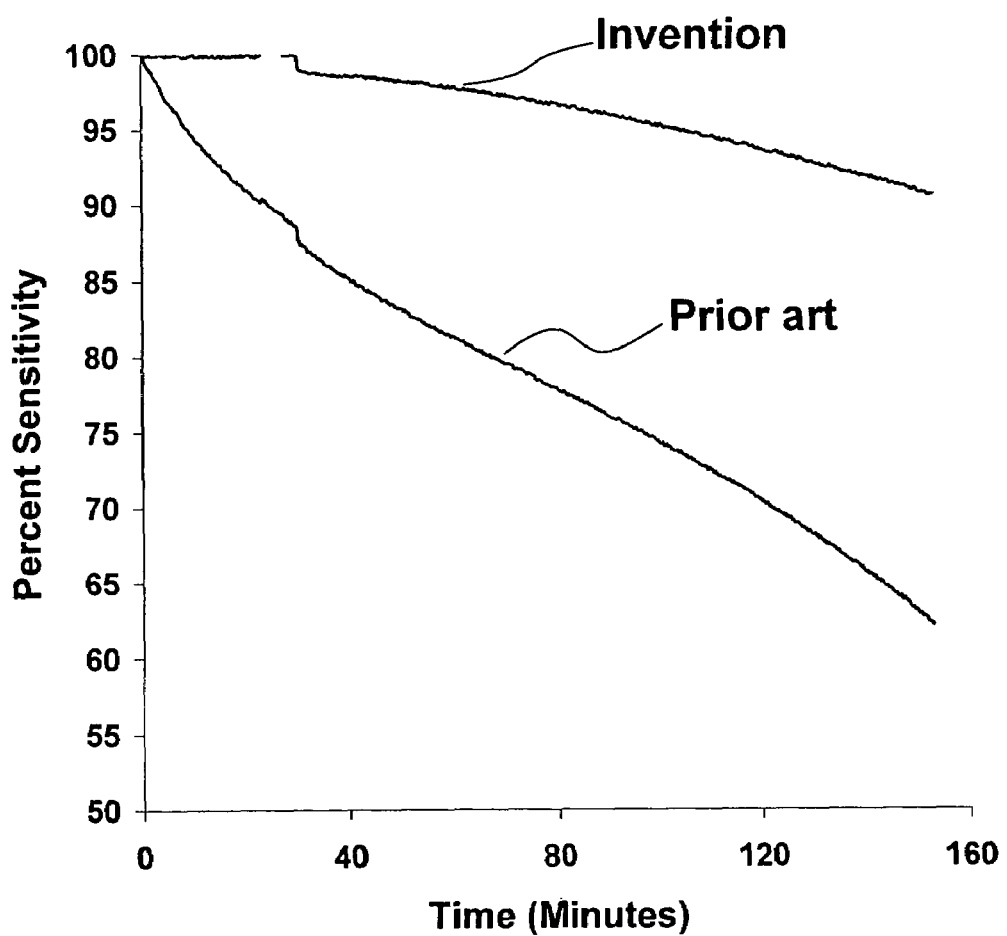
FIG. 7 is a graph illustrating the deactivation of a sensor made in accordance with the invention and a prior art sensor in the presence of 9.5 ppm hexamethyldisiloxane (HMDS) and 0.91 vol % methane in air.

FIG. 7 is a graph of sensitivity vs. time illustrating the results of a laboratory test in which a gas-sensing element with an outer layer of a porous alumina-supported cobalt oxide ($CoO_x/Al_2O_3$) made in accordance with the invention, and a gas-sensing element made in accordance with U.S. Pat. No. 4,123,225 are exposed to a gaseous mixture of 9.5 ppm by volume hexamethyldisiloxane (HMDS) and 0.91 vol % methane in air. The graph shows a marked difference in the rate of poisoning between the prior art gas-sensing element and that in accordance with the invention. The gas-sensing element of the invention exhibits substantially improved resistance to HMDS compared to the prior art sensor. The exceptionally high poison resistance of the gas-sensing element in accordance with this invention is believed to originate from the fact that the porous alumina-supported cobalt oxide ($CoO_x/Al_2O_3$) in the outer layer 22 is highly active and effective in trapping HMDS to prevent it from diffusing into the inner catalyst layer 21.

It is another general object of the invention to provide a method to warn the user that poisoning has occurred by determining a baseline drift when a catalytic bead sensor is exposed to poisons present in ambient air. This method is an inexpensive and effective diagnostic of sensor poisoning. When a sensor is poisoned, a dangerous situation can arise if the gas detection instrument is in use without the operator knowing the sensor is poisoned, because the sensor would fail to report an alarm in the presence of a combustible gas such as methane. The method according to the invention provides an early warning of poisoning of the sensor.

The sensors in accordance with the invention generally possess baseline drift in a negative direction when exposed to poisons. Thus, when a gas sensor is connected in an electric circuit such as a Wheatstone bridge circuit, a negative baseline drift is observed during poisoning, and the modification of the sensor that enhances the resistance of the sensor to poisoning also provides the means to detect when the sensor has been exposed to a substantial amount of poisons.

Figure 8:
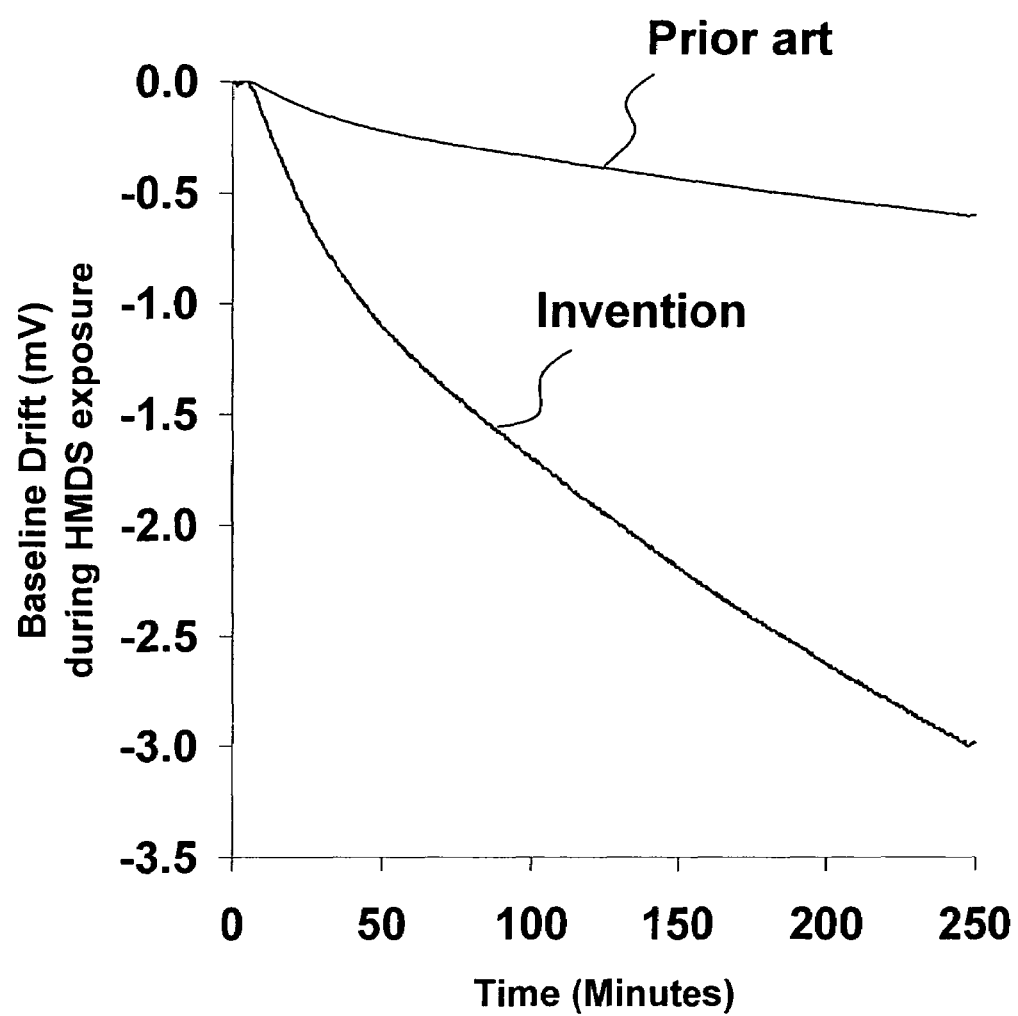
FIG. 8 is a graph showing negative baseline drift of a sensor made in accordance with the invention and a prior art sensor in the presence of 9.5 ppm hexamethyldisiloxane (HMDS) in air.

Referring to FIG. 8, there is illustrated a marked difference in baseline drift between a sensor in accordance with the invention (the sensor of FIG. 2) and a prior art sensor upon exposure to 9.5 ppm hexamethyldisiloxane (HMDS) in air for 4 hours. The negative baseline drift during HMDS poisoning can be used to warn of possible poisoning of a combustible gas sensor.

This aspect of the invention can be incorporated into a gas detection instrument to provide warning of poisoning. Once the baseline negatively drifts to such an extent within a given period of time that it reaches a predetermined level, the gas detection device can generate a warning signal that may be used to indicate the possible poisoning of the sensor to an operator.

Tests were carried out in which sensors according to the invention and prior art sensors were operated in gas detection instruments, and were exposed continuously to 9.5 ppm hexamethyldisiloxane (HMDS) in air for 4 hours. Table 1 below summarizes the baselines and responses to 1 vol % methane (i.e. 20% LEL, Low Explosive Limit) before and after flowing HMDS. After flowing HMDS, the baseline of the sensor in accordance with the invention negatively drifted to −5% LEL, much larger than that (−1% LEL) of the prior art sensor. It should be emphasized that the baseline drift of both the prior art sensor and the sensor in accordance with the invention would be negligible within this time period in the absence of poisoning materials. If the instrument detects a negative baseline drift large enough that it reaches a predetermined level within a given period of time (i.e. rate of baseline change), the instrument can generate a signal to indicate possible poisoning. It can also be seen from Table 1 that the response to 1 vol % methane (i.e. 20% LEL) of the sensor in accordance with this invention after flowing HMDS is 7% LEL, which is higher than that (3% LEL) of the prior art sensor, due to its high intrinsic resistance to HMDS.

TABLE 1

| Sensor type | Baseline before HMDS (% LEL) | 1% CH₄ reading before HMDS (% LEL) | Baseline after HMDS (% LEL) | 1% CH₄ reading after HMDS (% LEL) |
| --- | --- | --- | --- | --- |
| Prior art | 0 | 20 | −1 | 3 |
| Invention | 0 | 20 | −5 | 7 |

There are numerous advantages associated with warning of poisoning by the invention. For example, the invention provides an effective warning of a combustible gas sensor being poisoned without the necessity of checking the sensor response to a combustible test gas. The invention also enables a combustible gas detection device to have a diagnostic feature of warning for possible poisoning, which will definitely benefit safety and integrity of life-protection devices. Furthermore, the invention provides an inexpensive approach to warning of poisoning and reduces manual labor and costs needed with verifying that a gas detection device is not poisoned and will still respond in the event of gas leakage.

Table 2 below summarizes poisoning resistance and baseline drift of gas-sensing elements with different porous oxide-supported catalytic materials coating the outer layer 22 (FIG. 2) in accordance with the invention, after exposure to a gaseous mixture of 9.5 ppm hexamethyldisiloxane (HMDS) and 0.91 vol % methane in air. It can be seen that the poisoning resistance and baseline drift of these sensors substantially depend on the active components in the alumina-supported catalytic materials. The HMDS resistance follows the trend: Ni>Co, Cr>Cu>Mn, mesoporous $SO_4^{2-}$/$ZrO_2$>Fe>MgO. In comparison, sensors without the outer layer 22 gave a methane sensitivity loss of −60% initial signal after HMDS. The poisoning resistance and baseline drift during poisoning can be adjusted by varying the types and contents of active components, the oxide supports, and preparation methods.

TABLE 2

| Sensor No. | Outer layer material | Sensitivity loss (% initial signal) | Baseline drift (% initial signal) |
| --- | --- | --- | --- |
| 1 | None | −60 | −10 |
| 2 | alumina | −45 | −5 |
| 3 | Chromium oxide/alumina | −14 | −17 |
| 4 | Cobalt oxide/alumina | −11 | −15 |
| 5 | Copper oxide/alumina | −21 | −21 |
| 6 | Iron oxide/alumina | −40 | −16 |
| 7 | Manganese oxide/alumina | −31 | −13 |
| 8 | Nickel oxide/alumina | −8 | −4 |
| 9 | Magnesium oxide | −53 | −29 |
| 10 | Mesoporous sulfated zirconia | −34 | −19 |

Poison resistant gas-sensing elements according to the invention are further illustrated by, but not limited to, the following examples:

EXAMPLE 1

For fabricating the inner layer 21 of the gas-sensing element 10 in FIG. 2, a slurry "A" is first prepared by adding 0.2 g $PdCl_2$ and 2.0 g porous alumina into 25.0 ml de-ionized water. The slurry "A" is then applied to the coil 20, followed by passing a current through the coil to heat it to 500–700° C. to drive off the water from the slurry, consolidate the alumina deposit and decompose the palladium chloride to palladium oxide and metallic palladium. Multiple coats of slurry are applied and heated until a desired size is obtained. The resulting pellet "P" with only the inner layer 21 as a starting point in all examples.

For fabricating an outer layer 22 for the gas-sensing element 10, a porous alumina-supported cobalt oxide ($CoO_x$/$Al_2O_3$) is first prepared by incipient impregnation of 1.0 g porous alumina with 3.0 ml aqueous solution containing 0.3 g cobalt (II) chloride hexahydrate. The resulting paste is subsequently heated in an oven at 60° C. for 1.5 hrs, 120° C. for 1 hr and 650° C. for 2 hrs to completely decompose the cobalt (II) chloride hexahydrate to cobalt oxides supported on the surface of the alumina. Then, a slurry "B" is prepared by adding 0.3 g the above alumina-supported cobalt oxide ($CoO_x$/$Al_2O_3$) into 3.0 ml de-ionized water. The slurry "B" is applied onto the pellet "P" and heated to form the outer layer 22. More than one layer of slurry "B" can be applied to obtain a desired thickness of the outer layer 22.

For comparison, a prior art gas-sensing element 10 is fabricated by applying onto the pellet "P" a slurry "C" containing a mixture of alumina and aluminum nitrate as described in U.S. Pat. No. 4,123,225.

EXAMPLE 2

0.3 g mesoporous sulfated zirconia (32 Å), a solid superacidic material, is added to 3.0 ml de-ionized water to form a slurry "E", which is then applied onto a pellet "P" described in EXAMPLE 1 to form the outer layer 22. The formation of the gas-sensing element is otherwise carried out in the same manner as in EXAMPLE 1.

EXAMPLE 3

A solid base, magnesium oxide, is used to coat the inner layer 21 of a pellet "P" described in EXAMPLE 1 to form the outer layer 22. The manufacture processes of the gas-sensing element are otherwise the same as in EXAMPLE 1.

EXAMPLE 4

An external filter is made by absorbing a mixture of 0.3 g silver acetate, 0.2 g porous aluminum oxide, and 3.0 ml deionized water into a piece of glass fiber filter paper. The chemically treated glass fiber filter paper is then dried at room temperature. The active component in the filter is silver acetate salt supported on alumina; silver oxide is not activated since high temperature treatment is not applied. Test results show that the filter can significantly improve HMDS resistance, i.e. −26.9% sensitivity loss for a sensor with a filter versus −60.4% sensitivity loss for a sensor without a filter.

While preferred embodiments of this invention have been illustrated, it is to be understood that other modifications may be made within the scope of the appended claims. For example, an outer layer of inert non-catalytic material may be applied onto the outer layer of the sensing element of this invention, or alternating layers of inert non-catalytic material and active porous oxide-supported catalytic material described in this invention may be applied. For warning of poisoning, circuits other than the Wheatstone bridge circuit can be used to measure the difference in resistance between the gas-sensing element and the compensating element when the sensor is exposed to poisons. In addition to the gas-sensing element of the invention, the compensating element can also be made so that a whole sensor possesses a positive or negative baseline drift upon exposure to catalyst poisoning materials. The discussion herein is primarily directed to catalytic bead combustible gas sensors; however, the disclosure herein with respect to use of active catalytic materials as poison-capturing layers and changes in zero output for diagnostic is applicable to other types of gas sensors and detection devices, such as semiconductor sensors and apparatus for use therewith.

What is claimed is:

1. A method for determining poisoning of a gas sensing element comprising the steps of:
    a) forming an apparatus for detecting a combustible gas comprising:
        a gas sensing element including an electric heating element, a first layer coated on the electric heating element and comprising a precious metal catalyst supported on a porous oxide, the precious metal catalyst catalyzing combustion of a combustible gas to be detected by the sensing element, and a second layer overlaying the first layer, and comprising a catalytic compound capable of trapping gases which poison the precious metal catalyst, said catalytic compound being supported on a porous oxide;
        a compensating element comprising an electric heating element, said compensating element not including a catalyst capable of catalyzing combustion of a combustible gas to be detected by the sensing element; and
        an electrical circuit to which the sensing element and compensating element are connected, said electrical circuit being constructed and arranged to detect changes in resistance of the sensing element and compensating element, and to provide a reading of said changes;
    b) operating said apparatus in an atmosphere substantially without combustible gases to determine a baseline reading for said apparatus; and
    c) continuing to observe said baseline reading, with a drift of baseline indicating poisoning of said gas sensing element.

2. The method of claim 1, wherein the drift is a negative drift.

3. The method of claim 1, additionally comprising poisoning a second said gas sensing element, and determining the baseline drift of the poisoned gas sensing element for comparison with said observed baseline drift.

4. The method of claim 3, wherein said poisoning comprises exposing the gas sensing element to an organosilicon compound.

5. The method of claim 4, wherein the organosilicon compound is hexamethyldisiloxane.

* * * * *